(12) United States Patent
Russo et al.

(10) Patent No.: US 8,956,342 B1
(45) Date of Patent: Feb. 17, 2015

(54) METHOD AND DEVICE FOR ERGONOMICALLY AND AMBIDEXTROUSLY OPERABLE SURGICAL DEVICE

(75) Inventors: Robert Scott Russo, Charlottesville, VA (US); John H. Pascaloff, Charlottesville, VA (US); Robert McKemie, Charlottesville, VA (US)

(73) Assignee: Microaire Surgical Instruments LLC, Charlottesville, VA (US)

( * ) Notice: Subject to any disclaimer, the term of this patent is extended or adjusted under 35 U.S.C. 154(b) by 0 days.

(21) Appl. No.: 13/602,696

(22) Filed: Sep. 4, 2012

Related U.S. Application Data

(60) Provisional application No. 61/530,183, filed on Sep. 1, 2011, provisional application No. 61/603,718, filed on Feb. 27, 2012.

(51) Int. Cl.
*A61B 17/00* (2006.01)

(52) U.S. Cl.
USPC .............. 606/1; 606/130; 606/205; 403/4; 403/322.2; 408/144; 307/126; 310/50; 227/175.2

(58) Field of Classification Search
CPC ........ A61B 19/00; A61B 17/00; A61B 17/04; F16B 5/02; B23B 27/14; H01H 47/00; H02K 7/14

USPC ........... 606/130, 205; 403/4, 322.2; 408/144; 307/126; 310/50; 227/175.2, 178.1, 227/180.1

See application file for complete search history.

(56) References Cited

U.S. PATENT DOCUMENTS

| | | | | |
|---|---|---|---|---|
| 3,574,374 | A | * | 4/1971 | Keller et al. ................... 403/4 |
| 4,097,703 | A | * | 6/1978 | Houser ...................... 307/126 |
| 4,342,931 | A | * | 8/1982 | Grossmann et al. ........... 310/50 |
| 5,911,700 | A | * | 6/1999 | Mozsary et al. ............... 604/22 |
| 6,030,156 | A | * | 2/2000 | Andronica .................. 408/144 |
| 6,386,789 | B1 | * | 5/2002 | Chausse et al. ........... 403/322.2 |
| 7,770,775 | B2 | * | 8/2010 | Shelton et al. ............. 227/178.1 |
| 7,845,537 | B2 | * | 12/2010 | Shelton et al. ............. 227/180.1 |
| 7,959,050 | B2 | * | 6/2011 | Smith et al. ............... 227/175.2 |
| 2005/0222587 | A1 | * | 10/2005 | Jinno et al. ................. 606/130 |
| 2006/0243469 | A1 | * | 11/2006 | Webster ...................... 173/217 |
| 2008/0255420 | A1 | * | 10/2008 | Lee et al. .................... 600/137 |
| 2009/0069842 | A1 | * | 3/2009 | Lee et al. .................... 606/205 |

\* cited by examiner

*Primary Examiner* — William Thomson
*Assistant Examiner* — Victor Shapiro
(74) *Attorney, Agent, or Firm* — Suiter Swantz pc llo

(57) ABSTRACT

A handheld surgical device includes a multi-position throttle, rotatably attached to the body of the device, to allow for ambidextrous positioning of a motor speed control lever. The motor speed control lever may interact with a speed control sensor in the body of the device capable of detecting the actuation level of the motor speed control lever in any one of two or more positions.

20 Claims, 6 Drawing Sheets

METHOD AND DEVICE FOR ERGONOMICALLY AND AMBIDEXTROUSLY OPERABLE SURGICAL DEVICE

PRIORITY

The present application claims the benefit under 35 U.S.C. §119(e) of U.S. Provisional Application Ser. No. 61/530,183, filed Sep. 1, 2011, and U.S. Provisional Application Ser. No. 61/603,718, filed Feb. 27, 2012, which are incorporated herein by reference.

FIELD OF THE INVENTION

The present disclosure relates to the field of medical surgery and surgical devices and particularly to a handheld surgical device.

BACKGROUND

Promoting patient safety, mitigating patient injuries and are critical goals during surgical procedures. Cost-effective medical equipment purchasing is also important in the healthcare industry. Surgeons require tools suitable to their style and physiology. For example, left-handed surgeons may require slightly different tools as compared to right-handed surgeons for maximum efficiency.

Medical surgery may involve surgical procedures using handheld surgical devices. These types of surgery may include various orthopedic surgeries, soft-tissue surgeries, plastic surgeries, reconstructive surgeries, endoscopic surgeries, biopsy surgeries, transplant surgeries, and numerous other types of surgeries. These surgical procedures may include various means of altering tissue, tissue orientation, tissue location, bodily structures, bodily structure orientation, bodily structure location, foreign objects, foreign object orientation, or foreign object location such as by cutting, lasering, burning, removing, navigating, attaching, connecting, draining, implanting, transplanting, setting, separating, pulling, stretching, inserting, suturing, stitching, or stapling, or the like. All of these procedures may be time consuming and physically demanding for a surgeon.

Consequently a surgical device with an ergonomic, ambidextrously positionable motor speed lever and directional switches would be advantageous.

SUMMARY OF THE INVENTION

The present invention is directed toward a surgical device with an ergonomic, ambidextrously positionable motor speed lever and directional switches would be advantageous.

One embodiment of the present invention is a surgical device having a motor speed lever connected to a multi-position throttle. The multi-position throttle allows the motor speed lever to be positioned for left or right hand operation. The motor speed lever may interact with a speed control sensor configured to be useful with the motor speed lever in one of at least two different positions.

Another embodiment of the present invention is a surgical device having a motor speed lever connected to a multi-position throttle. The multi-position throttle may engage a run/safe sensor when the multi-position throttle is in a position designated as "safe," such that the surgical device will not operate.

BRIEF DESCRIPTION OF THE DRAWINGS

The numerous objects and advantages of the present invention may be better understood by those skilled in the art by reference to the accompanying figures in which.

DETAILED DESCRIPTION

Figure 1:
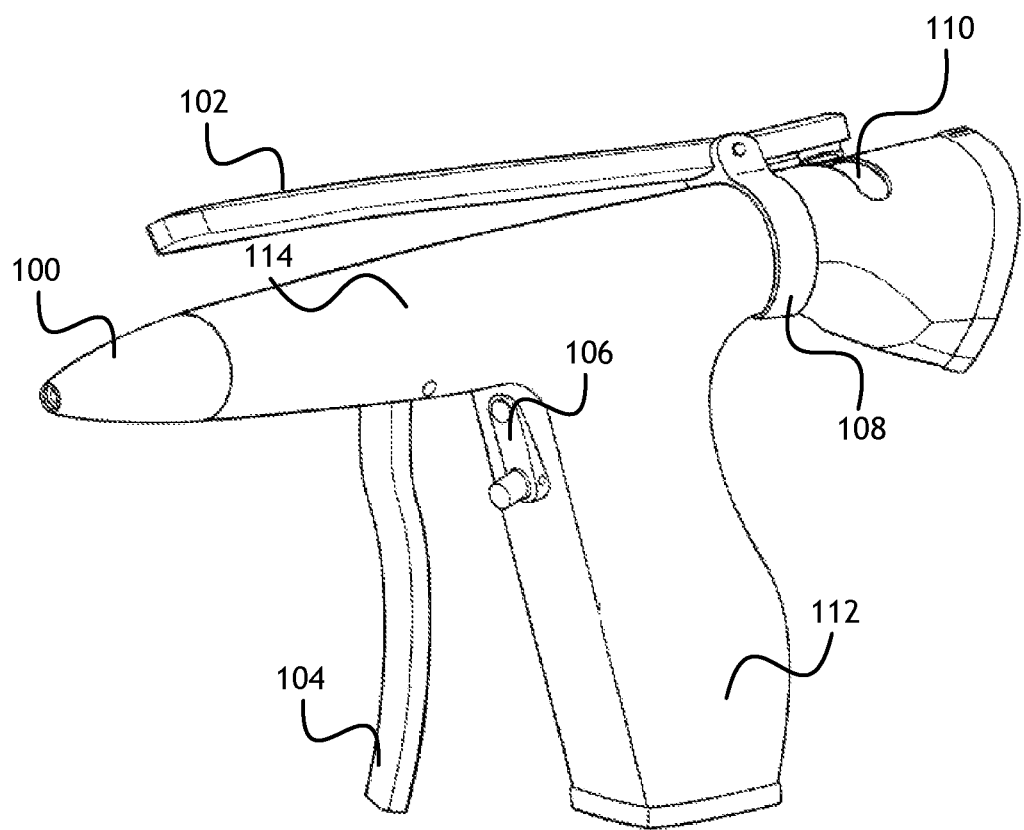
FIG. 1 shows an isometric view of a handheld pin/wire driver.

The risks of injuring a patient during surgery may be mitigated and accurate performance may be promoted in accordance with the present invention. Additionally, the present invention may mitigate the need to purchase multiple surgical devices.

Promoting patient safety and mitigating patient injuries are critical goals during surgical procedures. The present invention discloses solutions to prevent unintentional operation of a surgical device, to promote surgical accuracy, and to mitigate the possibility of patient injury and complications. The ergonomic design, weighting, maneuverability, and configuration enhance a surgeon's ability to perform technical surgical procedures. The invention also promotes improving and maintaining visibility at a surgical area during a surgical procedure.

The invention discloses solutions to improve and maintain visibility during surgical procedures.

Cost-effective medical equipment purchasing is important in the healthcare industry. The present invention may reduce the need to purchase multiple surgical devices or attachments by including a broad range of multi-functionality that can be used by right and left-handed surgeons.

Medical surgery may involve surgical procedures using handheld surgical devices which would benefit from a handheld ergonomically and ambidextrously operable surgical device. These types of surgery may include various orthopedic surgeries, soft-tissue surgeries, plastic surgeries, reconstructive surgeries, endoscopic surgeries, biopsy surgeries, transplant surgeries, and numerous other types of surgeries. Surgical procedures used in surgeries, which involve surgical procedures which may benefit from a handheld ergonomically and ambidextrously operable surgical device, may include diagnostic procedures, treatments, or methods of obtaining a desired medical effect. These surgical procedures may include various means of altering tissue, tissue orientation, tissue location, bodily structures, bodily structure orientation, bodily structure location, foreign objects, foreign object orientation, or foreign object location such as by cutting, lasering, burning, removing, navigating, attaching, connecting, draining, implanting, transplanting, setting, separating, pulling, stretching, inserting, suturing, stitching, or stapling, or the like. The disclosed invention contemplates including an ambidextrously positionable motor speed lever 102, directional switches, and a lever on handheld surgical devices for these surgical procedures to promote patient safety and cost effectiveness.

Reference will now be made in detail to the subject matter disclosed, which is illustrated in the accompanying drawings. Numerous alternatives, modifications, and equivalents are encompassed. For the purpose of clarity, technical material that is known in the technical fields related to the embodiments has not been described in detail to avoid unnecessarily obscuring the description.

Contemplated embodiments of the invention may include a handheld surgical device for performing surgical or medical procedures, such as a handheld pin/wire driver for driving pins, wires or small drills during small bone orthopedic surgeries.

Referring to FIG. 1, an isometric view of a handheld pin/wire driver is shown. A handheld pin/wire driver may comprise a handle 112; a driver body 114, wherein the driver body may be connected to the top of the handle and have a front end and rear end; an rocker-style motor speed lever 102 for motor speed control; a directional switch 106; a multi-position throttle 108 for the motor speed lever 102; and an actuation lever 104 for pin/wire gripping actuation. The motor speed lever 102 may engage a speed control sensor groove 110 that may allow the motor speed lever 102 to interact with a speed control sensor while the multi-position throttle 108 is in one of at least two different positions. The handheld pin/wire driver may further include a motor and allow for removable attachment of a rechargeable battery. The handheld pin/wire driver may be configured such that removably attachable attachment pieces may be connected to the handheld pin/wire driver at a removable front end cap 100. The handheld pin/wire driver may be autoclavable. The handheld pin/wire driver may also be configured to receive power, send analog signals or digital data streams, or receive analog signals or digital data streams via one or more cords.

The driver body 114 may comprise a slender body design with a tapering front end to promote improved visibility. The driver body may also include a pin/wire channel (defined herein) running from the front of the driver body to the rear end of the driver body. The pin/wire channel may be configured to receive pins or wires with diameters in a range of 0.6 mm to 3.2 mm. One advantage of the disclosed invention is that the disclosed pin/wire driver of this invention is capable of handling a broader range of pins/wires (i.e., 0.6 mm to 3.2 mm diameter) than other pin/wire drivers without requiring the purchase of multiple attachments. Furthermore, a surgeon would not have a need to stop mid-surgery to interchange attachment pieces of a pin/wire driver to accommodate a different diameter pin or wire. One skilled in the art may appreciate that the pin/wire diameter range 0.6 mm to 3.2 mm is exemplary.

The handheld pin/wire driver may be configured such that a location of the center of mass of the handheld pin/wire driver allows for easy maneuvering and operation of the handheld pin/wire driver. When a surgeon is operably gripping the handle 112 of the handheld pin/wire driver, the location of the center of mass of the handheld pin/wire driver may be configured such that the handheld pin/wire driver does not have a tendency to tilt forward, backward, or to the side. That is, the center of mass of the handheld pin/wire driver may be located so as to minimize torque moments when a surgeon is operably gripping the handle 112.

The handheld pin/wire driver may be configured such that an operator may hold the handle 112 of the handheld pin/wire driver with a hand, actuate and operate the actuation lever 104 with at least one finger of the same hand, and operate and actuate the motor speed lever 102 with at least another finger on the same hand.

Figure 2:
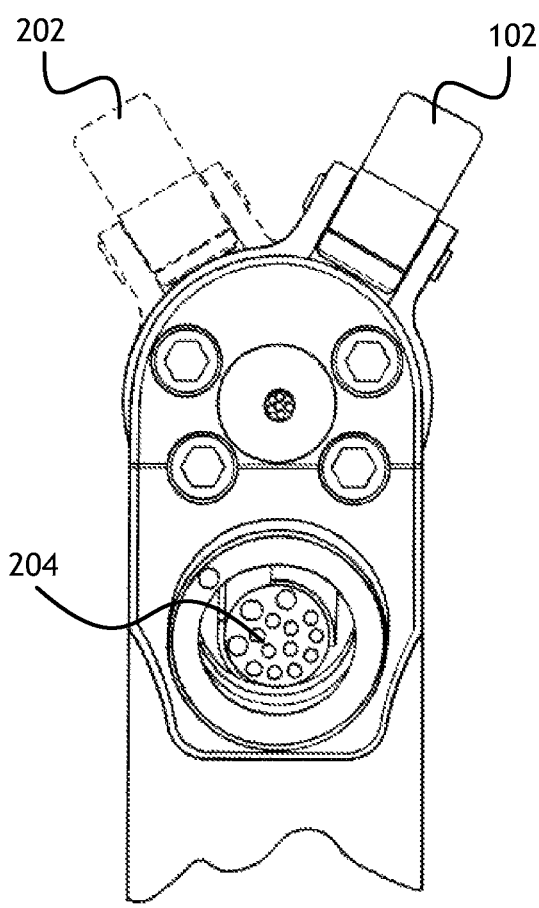
FIG. 2 shows a rear view of the handheld pin/wire driver of FIG. 1.

Referring to FIG. 2, a rear view of the handheld pin/wire driver in FIG. 1 is shown. The handheld pin/wire driver may be configured to be capable of communicating with a coupled control console via a cord through a power/data port 204. The handheld pin/wire driver may include at least one power/data port 204, wherein the power/data port 204 is capable of operatively engaging with a cord for receiving power, sending analog signals or digital data streams, or receiving analog signals or digital data streams. The handheld pin/wire driver may be configured to communicate with a control console, a computing product system, or an audio/visual display system via the power/data port and cord. The handheld pin/wire driver may further include a wireless card or wireless antenna (not shown) capable of sending and receiving wireless signals. Additionally, the handheld pin/wire driver may be configured to communicate wirelessly with a control console, a computing product system, or an audio/visual display system, or any control console, computing product system, or audio/visual display system connected to a network.

The motor speed lever 102 may be positionable relative to a handle such that an operator gripping the handle with the operator's right hand may actuate the motor speed level 102 with the operator's right hand index finger. Furthermore, the handheld pin/wire driver may include a multi-position throttle. The multi-position throttle of the handheld pin/wire driver may include a positionable ring. The positionable ring may be configured such that the positionable ring encompasses a band around the driver body. The positionable ring may be configured to rotate in a limited range around the driver body. The multi-position throttle may be rotated to one of at least two positions by sliding the positionable ring around driver body from at least a first position to at least a second position, or vice versa. Because the motor speed lever 102 may be connected to the multi-position throttle, and therefore the positionable ring, the motor speed lever 102 may be placed in at least two positions. For example, the multi-position throttle may include three positions: a right-handed position configured (illustrated by the motor speed lever 102) for right-handed operation of the motor speed lever, a left-handed position 202 configured for left-handed operation of the motor speed lever 102, and a safe mode position (not shown) whereby the handheld pin/wire driver does not operably respond to actuation of the motor speed lever 102.

Figure 3:
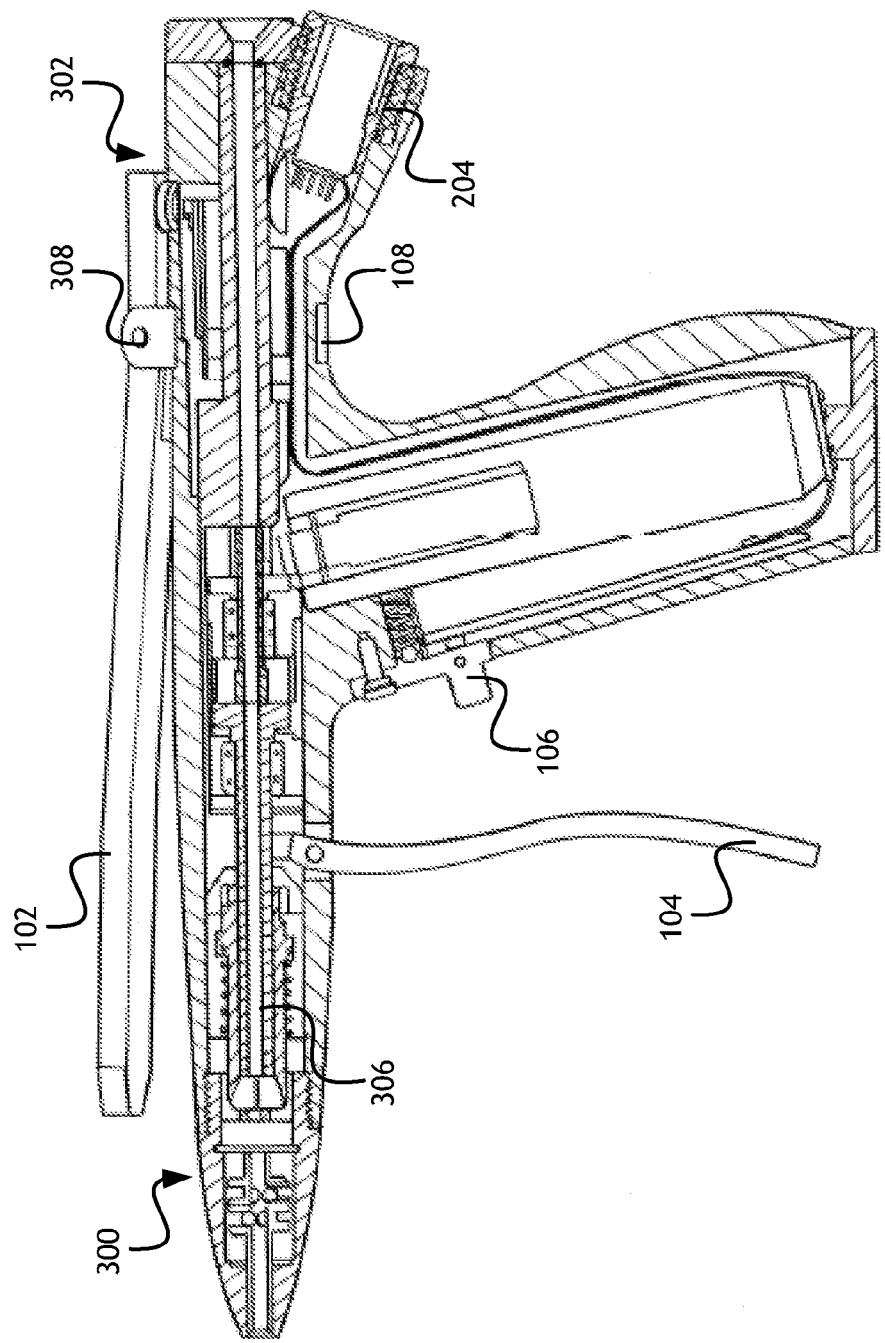
FIG. 3 shows a cross-sectional side view of the handheld pin/wire driver of FIG. 1.

Referring to FIG. 3, a cross-sectional side view of the handheld pin/wire driver in FIG. 1 is shown. The handheld pin/wire driver may include a front-end portion 300 and a back-end portion 302 further detailed herein. The handheld pin/wire driver may include a motor speed lever 102 connected to a multi-position throttle 108 at an attachment point 308. The handheld pin/wire driver may define a pin/wire receiving channel 306 that may allow appropriate surgical implements to progress when driven by a drive mechanism.

The motor speed lever 102 may be configured to be ambidextrously positionable. The motor speed lever 102 for controlling motor speed may be connected with a pin to the attachment point 308 on the multi-position throttle 108. The motor speed lever 102 may be configured to variably control the speed of operation of a motor. The orientation of the motor speed lever 102 may be positioned to accommodate either left or right-handed surgeons by sliding the positionable ring of the multi-position throttle around the driver body to either the left-handed position or the right-handed position. When the motor speed lever 102 is in either the right-handed or left-handed position, the rear end of the motor speed lever 102 may be configured to be in operable association with one or more speed control sensors (described herein) located beneath an exterior layer of the driver body. When the motor speed lever 102 is in the safe mode position, the rear end of the motor speed lever 102 may be configured to be in inoperable association with one or more speed control sensors located beneath an exterior layer of the driver body.

The handheld pin/wire driver may also include a directional switch 106. The directional switch 106 may allow a surgeon to set a motor to drive in a forward, reverse, or oscillating direction. The directional switch 106 may be located on a front upper portion of the handle below the driver body. This location of the directional switch 106 may prevent the directional switch 106 from accidental switch change. The directional switch 106 may further be configured such that the direction of the directional switch 106 may not be changed during operation of the motor.

Figure 4:
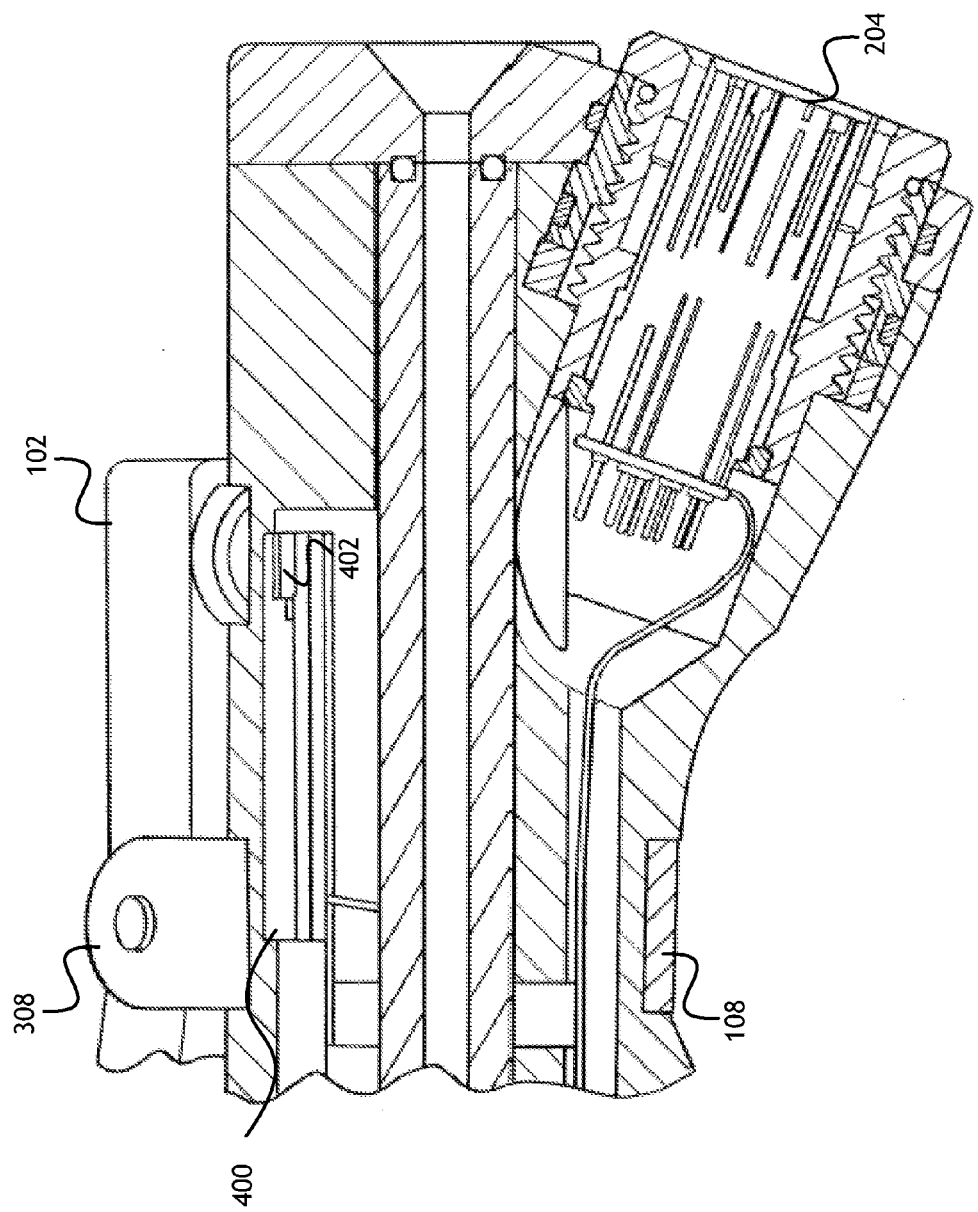
FIG. 4 shows a cross-sectional, close-up side view of a rear portion of the handheld pin/wire driver of FIG. 3.

Referring to FIG. 4, a cross-sectional, close-up side view of a rear portion of the handheld pin/wire driver of FIG. 3 is shown. A handheld pin/wire driver having a multi-position throttle 108 connected to a motor speed lever 102 through an attachment point 308 may further include a speed control sensor 402. The speed control sensor 402 may detect the degree to which the motor speed lever 102 is actuated. The speed control sensor 402 may be a mechanical device connected to the motor speed lever 102 or an electronic device configured to interact with the motor speed lever 102, for example through a magnet affixed to the motor speed lever 102. A person skilled in the art may appreciate that while a speed control sensor 402 is shown in the rear portion of the handheld pin/wire driver, the speed control sensor 402 may positioned anywhere where it is capable of sensing the level of actuation of the motor speed lever 102. In some embodiments, the speed control sensor may be located in the driver body and may further be configured to rotate with or in relation to the positionable ring.

The handheld pin/wire driver may further include a run/safe sensor 400. The run/safe sensor 400 may detect when a mechanism on the handheld pin/wire driver has been actuated to indicate that the motor in the handheld pin/wire driver should not be activated. For example, the run/safe sensor 400 may detect that the multi-position throttle 108 is in a position indicating a safe state. The run/safe sensor 400 may be a mechanical device engaging the multi-position throttle 108, an electronic device suitable for detecting the position of the multi-position throttle 108 or any other suitable mechanism.

Figure 5:
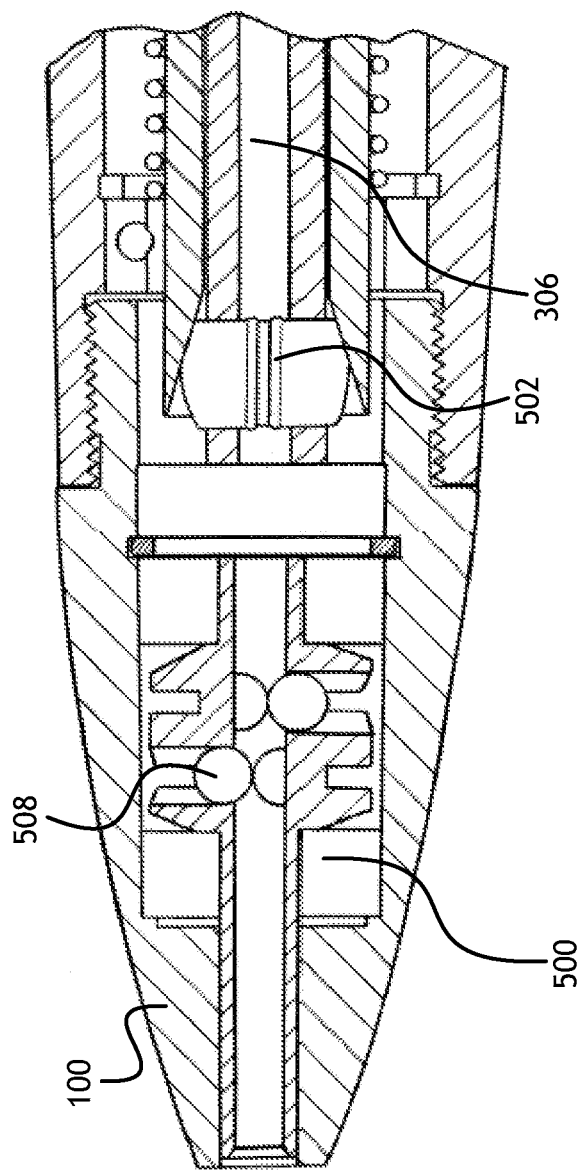
FIG. 5 shows a cross-sectional, close-up side view of a front portion of the handheld pin/wire driver of FIG. 3.

Referring to FIG. 5, a cross-sectional, close-up side view of a front portion of the handheld pin/wire driver of FIG. 3 is shown. A handheld pin/wire driver may include a gripper mechanism 502 and a guide mechanism 500. The guide mechanism 500 may be housed inside a removable front end cap 100. The gripper mechanism 502 and guide mechanism 500 may be configured to handle a range of pin and wire diameters. The guide mechanism 500 may include one or more pin or wire centering mechanisms 508. The centering mechanisms 508 may facilitate movement of a pin or wire through a pin/wire channel 306 by keeping the pin or wire in the center of the pin/wire channel 306, at least in the vicinity of the guide mechanism 500. The centering mechanism 508 may comprise a series of ball bearings positioned around the perimeter of the pin/wire channel 306 in the guide mechanism 500, each ball bearing spring biased toward the center of the pin/wire channel 306.

The gripper mechanism 502, when activated, may be configured to grip a pin or wire in the pin/wire channel 306 so as to prevent the pin or wire from sliding through the pin/wire channel 306. The handheld pin/wire driver may further include an actuation lever as illustrated in FIG. 1 for pin or wire gripping actuation. The gripper mechanism 502 may be in operable association with the actuation lever, such that when the actuation lever is actuated it may cause the gripper mechanism 502 to apply restrictive friction to a pin or wire in the pin/wire channel. The gripper mechanism 502 may comprise a single set of rectangular gripping blocks which force the pin or wire to align with the center axis of the pin/wire channel during clamping actuation.

The guide mechanism 500 may comprise two sets of opposing ball positioners for guiding wires or pins of different diameters through the pin/wire channel 306. The guide mechanism 500, when the gripper mechanism 502 is activated or inactivated, may be configured to grip a pin or wire in the pin/wire channel 306 so as to prevent the pin or wire from sliding through the pin/wire channel 306 under its own weight.

Figure 6:
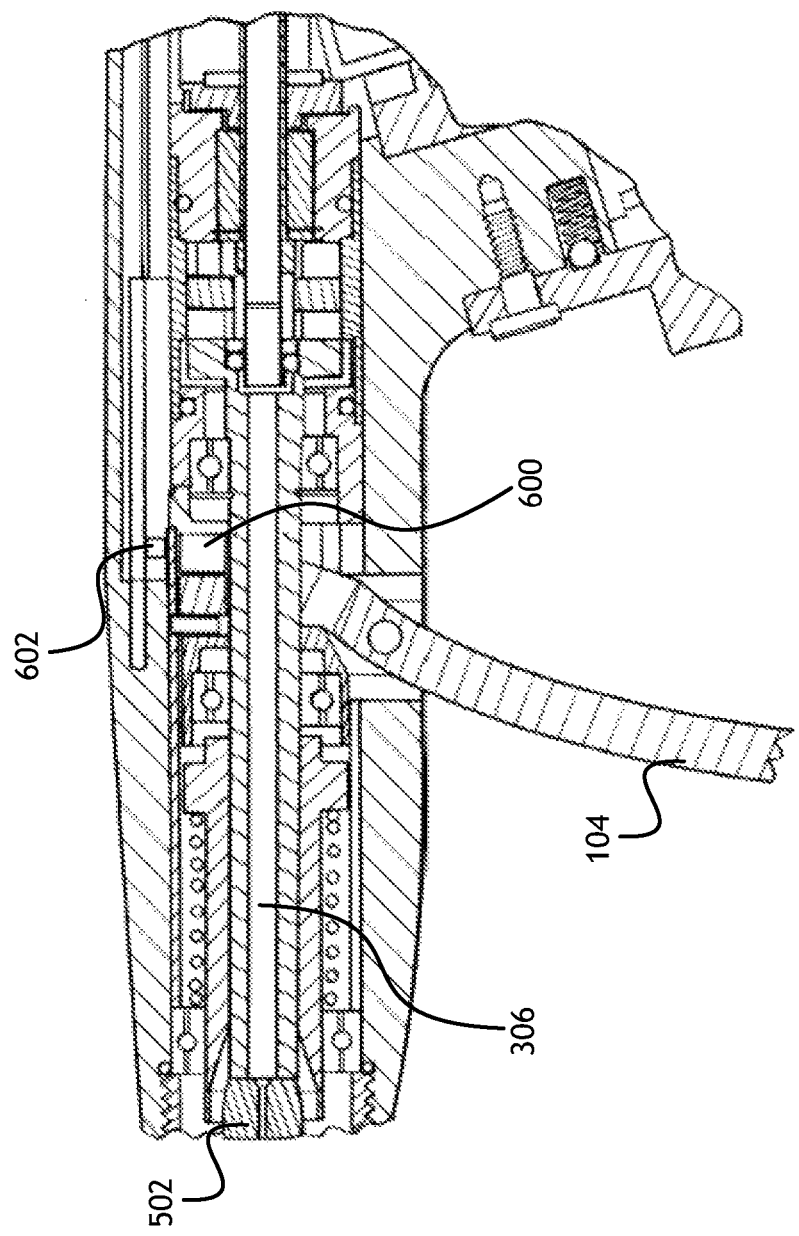
FIG. 6 shows a cross-sectional, close-up side view of a portion of the handheld pin/wire driver.

Referring to FIG. 6, a cross-sectional, close-up side view of a portion of the handheld pin/wire driver is shown. In one embodiment, when a gripper mechanism 502 is utilized to secure a pin or wire, a corresponding movement of a clamp positioner 600, such as a magnet may be effected. The clamp positioner 600 may be connected to an actuation lever 104 used to activate the gripper mechanism 502. A safety switch sensor 602 may detect the position of the clamp positioner 600 and may allow operation of a motor speed lever to control motor speed, or electronically activate a speed control sensor to so that actuation of a corresponding motor speed lever may send input to the speed control sensor and thereby control motor speed. In one embodiment, the safety switch sensor 602 may only allow throttle control when the clamp positioner 600 is measured past a threshold value. In one embodiment, as the clamp positioner 600 may be a magnet, a threshold value may refer to a detected magnetic field. Advantageously, use of the clamp positioner 600 and safety switch sensor 602 may prevent unintended or undesirable motor motion when the gripper mechanism 502 is not in a position for securing a pin or wire.

Other contemplated embodiments may include handheld medical or surgical devices configured to be used during other surgeries or surgical procedures described above. One skilled in the art may appreciate that while handheld pin/wire drivers have been specifically described, the same principles may apply to any handheld surgical instrument wherein one handed operation is desirable.

What is claimed is:

1. A handheld surgical apparatus comprising:
a motor speed lever;
a motor speed sensor configured to sense an actuation level of the motor speed lever; and
a positioning mechanism comprising a positionable ring connected to the motor speed lever,
wherein the positioning mechanism is configured to place the motor speed lever into at least a first orientation range aligning to a user's left index finger with one or more motor speed sensors configured for left-hand operation and a second orientation range aligning to a user's right index finger with one or more motor speed sensors configured for right-hand operation.

2. The apparatus of claim 1, further comprising:
a handle; and
a tool body connected to the handle,
wherein the positioning mechanism substantially circumscribed at least a portion of the tool body.

3. The apparatus of claim 2, further comprising a directional switch substantially positioned along a centerline of the handle, wherein the direction switch is configured for ambidextrous operation.

4. The apparatus of claim 2, wherein the tool body defines a channel configured for directing surgical implements.

5. The apparatus of claim 4, further comprising an actuation lever connected to the tool body, wherein the actuation lever is configured to actuate a drive mechanism, and configured for ambidextrous operation.

6. The apparatus of claim 5, further comprising a safety switch sensor configured to:
   determine the position of the actuation lever;
   deactivate the motor speed sensor when the actuation lever is in a first position; and
   activate the motor speed sensor when the actuation lever is in a second position.

7. The apparatus of claim 2, further comprising a power/data port connected to the tool body, wherein the power/data port is configured to transfer at least one of electrical power and data between the handheld surgical apparatus and a computing device.

8. The apparatus of claim 1, further comprising an integrated run/safe sensor, wherein:
   the positioning mechanism is further configured to place the motor speed lever into a third orientation;
   the third orientation is configured to activate the integrated run/safe sensor; and
   the integrated run/safe sensor is configured to prevent activation of a motor.

9. A handheld surgical apparatus comprising:
   a motor speed lever;
   an integrated run/safe sensor configured to prevent activation of a motor; and
   a positioning mechanism comprising a positionable ring connected to the motor speed lever,
   wherein the positioning mechanism is configured to place the motor speed lever into at least a first orientation range aligning to a user's left index finger with one or more motor speed sensors configured for left-hand operation and a second orientation range aligning to a user's right index finger with one or more motor speed sensors configured for right-hand operation and a third orientation configured to activate the integrated run/safe sensor.

10. The apparatus of claim 9, further comprising:
    a handle; and
    a tool body connected to the handle,
    wherein the positioning mechanism substantially circumscribes at least a portion of the tool body.

11. The apparatus of claim 10, further comprising a directional switch substantially positioned along a centerline of the handle, wherein the directional switch is configured for ambidextrous operation.

12. The apparatus of claim 10, wherein the tool body defines a channel configured for directing surgical implements.

13. The apparatus of claim 12, further comprising an actuation lever connected to the tool body, wherein the actuation lever is configured to actuate a drive mechanism, and configured for ambidextrous operation.

14. The apparatus of claim 10, further comprising a power/data port connected to the tool body, wherein the power/data port is configured to transfer at least one of electrical power and data between the handheld surgical apparatus and a computing device.

15. The apparatus of claim 9, further comprising a motor speed sensor configured to sense an actuation level of the motor speed lever.

16. A handheld surgical apparatus comprising:
    a handle;
    a tool body connected to the handle;
    a positioning mechanism comprising a positionable ring configured to rotatably circumscribe at least a portion of the tool body;
    a motor speed lever connected to the positioning mechanism;
    a motor speed sensor configured to sense an actuation level of the motor speed lever; and
    an integrated run/safe sensor configured to prevent activation of a motor,
    wherein the positioning mechanism is configured to place the motor speed lever into at least a first orientation range aligning to a user's left index finger with one or more motor speed sensors configured for left-hand operation and a second orientation range aligning to a user's right index finger with one or more motor speed sensors configured for right-hand operation and a third orientation configured to activate the integrated run/safe sensor.

17. The apparatus of claim 16, wherein the tool body defines a channel configured for directing surgical implements.

18. The apparatus of claim 17, further comprising an actuation lever connection to the tool body, wherein the actuation lever is configured to actuate a drive mechanism, and configured for ambidextrous operation.

19. The apparatus of claim 16, further comprising a power/data port connected to the tool body, wherein the power/data port is configured to transfer at least one of electrical power and data between the handheld surgical apparatus and a computing device.

20. The apparatus of claim 16, wherein the tool body is configured to provide a minimally obstructed line of sight corresponding to a surgical treatment section to be inserted into a subject body of site.

\* \* \* \* \*